United States Patent
Gassner et al.

(10) Patent No.: US 10,507,062 B2
(45) Date of Patent: Dec. 17, 2019

(54) MEDICAL FASTENING DEVICE AND REFERENCING DEVICE AND MEDICAL INSTRUMENTATION

(71) Applicant: Aesculap AG, Tuttlingen (DE)

(72) Inventors: Stefan Gassner, Immendingen-Hattingen (DE); Steffi Altmann, Donaueschingen (DE); Markus Mueller, Albstadt (DE)

(73) Assignee: Aesculap AG, Tuttlingen (DE)

( * ) Notice: Subject to any disclaimer, the term of this patent is extended or adjusted under 35 U.S.C. 154(b) by 527 days.

(21) Appl. No.: 15/278,154

(22) Filed: Sep. 28, 2016

(65) Prior Publication Data
US 2017/0209222 A1    Jul. 27, 2017

Related U.S. Application Data

(63) Continuation of application No. PCT/EP2015/056383, filed on Mar. 25, 2015.

(30) Foreign Application Priority Data

Apr. 3, 2014    (DE) .......................... 10 2014 104 800

(51) Int. Cl.
*A61B 34/20*     (2016.01)
*A61B 17/132*    (2006.01)
*A61B 90/00*     (2016.01)
*A61B 17/00*     (2006.01)

(52) U.S. Cl.
CPC .......... *A61B 34/20* (2016.02); *A61B 17/1322* (2013.01); *A61B 90/39* (2016.02);
(Continued)

(58) Field of Classification Search
CPC ..... A61B 34/20; A61B 90/39; A61B 17/1322; A61B 2034/2055; A61B 2090/3983; A61B 2090/3991; A61B 2017/00858
See application file for complete search history.

(56) References Cited

U.S. PATENT DOCUMENTS 1,428,465 A  *   9/1922   Willmott ................. D04B 1/24
                                                      450/75
1,445,840 A  *   2/1923   Malcolm ................. A61F 5/03
                                                      450/130
(Continued)

FOREIGN PATENT DOCUMENTS

CN       201167953       12/2008
CN       101801673       8/2010
(Continued)

OTHER PUBLICATIONS

Wikipedia entry for "Mannschaftskapitän", retrieved from the Internet, [retrieved on May 19, 2015],<URL:http://de.wikipedia.org/w/index.php?title=Mannschaftskapit%C3%A4n&oldid=125665552>, 4 pages.

(Continued)

*Primary Examiner* — Manav Seth
(74) *Attorney, Agent, or Firm* — Lipsitz & McAllister, LLC (57) ABSTRACT

A medical fastening device for noninvasively fastening a medical marking device comprising two or more marking elements to a body part of a patient is provided. The fastening device has a support body which extends over a surface in two directions of extent aligned at an angle to each other and is adaptable in its shape to the contour of the body part, to which the marking device is fixed or fixable. The support body is elastically stretchable in the surface of its extent and comprises a first stretch area and at least one second stretch area, the stretchability of which in at least one direction in the surface of the extent of the support body is less than that of the first stretch area. A medical referencing device and a medical instrumentation comprising such a fastening device are also provided.

22 Claims, 5 Drawing Sheets

(52) U.S. Cl.
 CPC .............. *A61B 2017/00858* (2013.01); *A61B 2034/2055* (2016.02); *A61B 2090/3983* (2016.02); *A61B 2090/3991* (2016.02)

(56) References Cited

U.S. PATENT DOCUMENTS

| | | | | |
|---|---|---|---|---|
| 1,985,210 | A * | 12/1934 | Krissiep | D04B 11/00 66/172 E |
| 2,246,246 | A * | 6/1941 | Gastrich | D04B 1/26 66/173 |
| 2,301,541 | A * | 11/1942 | Herb | D04B 1/26 66/172 E |
| 2,977,782 | A * | 4/1961 | Sheek | A41B 11/12 2/DIG. 9 |
| 3,375,530 | A * | 4/1968 | Matthews | A41B 9/001 2/402 |
| 3,421,503 | A * | 1/1969 | Kaplan | A61F 13/066 2/239 |
| 3,667,462 | A * | 6/1972 | Moon | A61F 13/00038 128/DIG. 15 |
| 3,831,467 | A * | 8/1974 | Moore | A61F 5/0109 602/26 |
| 4,492,227 | A | 1/1985 | Senn et al. | |
| 4,614,179 | A * | 9/1986 | Gardner | A61H 9/0078 128/DIG. 20 |
| 5,125,116 | A * | 6/1992 | Gaither | A41B 11/00 2/239 |
| 5,216,700 | A | 6/1993 | Cherian | |
| 5,261,871 | A * | 11/1993 | Greenfield | A61F 5/0109 602/19 |
| 5,306,229 | A * | 4/1994 | Brandt | A61F 5/0109 602/26 |
| 5,376,067 | A * | 12/1994 | Daneshvar | A61B 17/1322 602/13 |
| 5,497,513 | A * | 3/1996 | Arabeyre | A61F 13/08 2/16 |
| 5,540,063 | A * | 7/1996 | Ferrell | D04B 1/106 66/172 E |
| 6,050,967 | A | 4/2000 | Walker et al. | |
| 6,117,121 | A * | 9/2000 | Faulks | A61F 13/49017 604/385.29 |
| 6,149,616 | A * | 11/2000 | Szlema | A61F 13/061 602/26 |
| 6,279,579 | B1 | 8/2001 | Riaziat et al. | |
| 7,204,254 | B2 | 4/2007 | Riaziat et al. | |
| 7,757,518 | B2 * | 7/2010 | Sho | A41B 11/02 66/178 A |
| 7,853,311 | B1 | 12/2010 | Webb | |
| 7,882,713 | B2 * | 2/2011 | Tseng | D04B 1/18 66/172 E |
| 8,483,434 | B2 | 7/2013 | Buehner et al. | |
| 8,905,657 | B2 | 12/2014 | Grunenberg et al. | |
| 9,125,624 | B2 | 9/2015 | Dekel et al. | |
| 9,232,637 | B2 * | 1/2016 | Van Abeelen | D04B 1/12 |
| 9,408,752 | B2 * | 8/2016 | Oka | A61F 13/02 |
| 9,422,095 | B2 | 8/2016 | Grunenberg et al. | |
| 9,713,551 | B2 * | 7/2017 | Capobianco | A61F 13/0236 |
| 9,782,229 | B2 | 10/2017 | Crawford et al. | |
| 9,795,171 | B2 * | 10/2017 | Lipshaw | A41B 11/00 |
| 9,833,351 | B2 * | 12/2017 | Arbesman | A61F 5/0106 |
| 9,861,531 | B2 * | 1/2018 | Cobanoglu | A61F 13/00038 |
| 9,867,669 | B2 | 1/2018 | Zhao et al. | |
| 10,137,052 | B2 * | 11/2018 | Avitable | A61H 9/0078 |
| 2002/0023652 | A1 | 2/2002 | Riaziat et al. | |
| 2003/0019252 | A1 * | 1/2003 | Sciacca | D04B 1/243 66/171 |
| 2003/0065357 | A1 | 4/2003 | Dedo et al. | |
| 2004/0106861 | A1 | 6/2004 | Leitner | |
| 2004/0147839 | A1 | 7/2004 | Moctezuma de la Barrera et al. | |
| 2005/0026539 | A1 * | 2/2005 | Mitchell | A41C 3/0014 450/1 |
| 2005/0049485 | A1 | 3/2005 | Harmon et al. | |
| 2005/0245820 | A1 | 11/2005 | Sarin | |
| 2007/0244386 | A1 | 10/2007 | Steckner et al. | |
| 2008/0021309 | A1 | 1/2008 | Amiot et al. | |
| 2009/0018445 | A1 | 1/2009 | Schers et al. | |
| 2009/0043232 | A1 * | 2/2009 | Borschneck | A61F 5/0125 602/5 |
| 2009/0124949 | A1 | 5/2009 | Rosen | |
| 2009/0276939 | A1 * | 11/2009 | Sho | A41B 11/02 2/239 |
| 2010/0016771 | A1 * | 1/2010 | Arbesman | A61F 5/0106 602/5 |
| 2010/0106070 | A1 * | 4/2010 | Schlomski | A61F 5/0109 602/63 |
| 2010/0160932 | A1 | 6/2010 | Gschwandtner et al. | |
| 2010/0168763 | A1 | 7/2010 | Zhao et al. | |
| 2010/0189488 | A1 | 7/2010 | Grunenberg et al. | |
| 2010/0192961 | A1 * | 8/2010 | Amiot | A61G 13/12 128/882 |
| 2011/0004224 | A1 | 1/2011 | Daigneault et al. | |
| 2011/0069867 | A1 | 3/2011 | Buehner et al. | |
| 2011/0105828 | A1 * | 5/2011 | Perless | A61N 2/06 600/15 |
| 2012/0143050 | A1 | 6/2012 | Heigl | |
| 2013/0006120 | A1 | 1/2013 | Druse et al. | |
| 2013/0322719 | A1 | 12/2013 | Dekel et al. | |
| 2013/0334084 | A1 * | 12/2013 | Arbesman | A61F 13/025 206/441 |
| 2014/0128819 | A1 * | 5/2014 | Eaves | A61B 17/085 604/264 |
| 2014/0180182 | A1 * | 6/2014 | Collins | D04B 1/18 601/84 |
| 2014/0213843 | A1 * | 7/2014 | Pilla | A61N 2/006 600/14 |
| 2014/0213956 | A1 * | 7/2014 | Arbesman | A61F 5/0106 602/60 |
| 2014/0371650 | A1 * | 12/2014 | Cobanoglu | A61F 13/00038 602/43 |
| 2015/0164608 | A1 | 6/2015 | Bartenstein | |
| 2015/0304634 | A1 | 10/2015 | Karvounis | |
| 2016/0157938 | A1 | 6/2016 | Breisacher et al. | |
| 2016/0249988 | A1 | 9/2016 | Pfeifer et al. | |
| 2016/0361014 | A1 * | 12/2016 | Kane | A61B 5/1121 |
| 2017/0202634 | A1 * | 7/2017 | Gassner | A61B 34/20 |
| 2017/0340469 | A1 * | 11/2017 | Huffa | A61F 5/0109 |
| 2018/0071033 | A1 | 3/2018 | Zhao et al. | |

FOREIGN PATENT DOCUMENTS

| | | |
|---|---|---|
| CN | 102258399 | 11/2011 |
| CN | 102341054 | 2/2012 |
| CN | 102727308 | 10/2012 |
| DE | 20315470 | 1/2004 |
| DE | 10335595 | 2/2004 |
| DE | 69925010 | 3/2006 |
| DE | 202008003637 | 6/2008 |
| DE | 102010011589 | 9/2011 |
| EP | 1518508 | 3/2005 |
| EP | 2198801 | 6/2010 |
| EP | 2298215 | 3/2011 |
| EP | 1673146 | 11/2012 |
| GB | 2391814 | 2/2004 |
| WO | 01/21084 | 3/2001 |
| WO | 2009/059434 | 5/2009 |
| WO | 2009/111888 | 9/2009 |
| WO | 2011/023232 | 3/2011 |
| WO | 2011113482 | 9/2011 |
| WO | 2012/068679 | 5/2012 |
| WO | 2014/009967 | 1/2014 |
| WO | 2015/024600 | 2/2015 |

OTHER PUBLICATIONS

International Search Report for corresponding application No. PCT/EP2015/056383 dated Jun. 25, 2015, 3 pages.

* cited by examiner

MEDICAL FASTENING DEVICE AND REFERENCING DEVICE AND MEDICAL INSTRUMENTATION

CROSS-REFERENCE TO RELATED APPLICATIONS

This application is a continuation of international application number PCT/EP2015/056383 filed on Mar. 25, 2015 and claims the benefit of German application No. 10 2014 104 800.8 filed on Apr. 3, 2014, which are incorporated herein by reference in their entirety and for all purposes.

FIELD OF THE INVENTION

The present invention relates to a medical fastening device for noninvasively fastening a medical marking device comprising two or more marking elements to a body part of a patient, in particular, to a thigh, the fastening device comprising a support body which extends over a surface in two directions of extent aligned at an angle to each other and is adaptable in its shape to the contour of the body part, to which the marking device is fixed or fixable.

The invention also relates to a medical referencing device with a fastening device and a marking device.

The invention furthermore relates to a medical instrumentation.

BACKGROUND OF THE INVENTION

Medical referencing devices, which are used, for example, in knee prosthetics to make it easier for a surgeon to implant an artificial knee joint, are known.

The referencing device comprises the marking device with marking elements arranged rigidly relative to one another (so-called "rigid body") whose movement in space is tracked by a navigation system. To achieve as high an accuracy as possible, the marking device is screwed with a fastening device usually a bone screw, to the femur bone or to the tibia bone and thereby firmly fixed to it. However, this results in an intervention with a not inconsiderable degree of invasiveness about which some surgeons and patients have reservations.

To reduce the invasiveness, it is known to fix rigid bodies on a sleeve placed around the femur (in this case, thigh) or the tibia (in this case, lower leg) or to mount them on a plate placed on the femur or the tibia, which is fixed with bands to the respective body part. The sleeve comprises or forms a fastening device of the kind mentioned at the outset with a support body extending over a surface, which can undergo deformation from its originally planar shape and be adapted to the contour of the body part (for example, the femur or the tibia), so as to enable a positive fit on the body part.

Support bodies, which can be adhesively connected to the body part and to which the marking device is fixed, are also known.

With such noninvasive fastening devices, the problem occurs in practice that movements of the skin and muscles and soft tissue displacements, in particular, when movement of the body part in space is to be detected, are transmitted via the support body to the marking device. The accuracy of the position data of the marking device—and hence of the body part—on which the navigation-supported operation is to be based, is thereby impaired.

It would also be desirable to preoperatively and postoperatively detect patient data with a medical navigation system via a fastening device noninvasively attachable to the body part. Surgery times can thereby be reduced because data required therefore are already available preoperatively and need not first be determined intraoperatively. The success of the operation can be easily monitored postoperatively. In both cases, ionizing imaging procedures otherwise used, such as X-ray or CT, can be replaced.

An object underlying the present invention is to provide a generic fastening device, a referencing device and an instrumentation, with the use of which the noninvasively obtained position data have a higher accuracy.

SUMMARY OF THE INVENTION

In a first aspect of the invention, a medical fastening device is provided for noninvasively fastening a medical marking device comprising two or more marking elements to a body part of a patient, in particular, to a thigh. The fastening device comprises a support body which extends over a surface in two directions of extent aligned at an angle to each other and is adaptable in its shape to the contour of the body part, to which the marking device is fixed or fixable. The support body is elastically stretchable in the surface of its extent and comprises a first stretch area and at least one second stretch area, the stretchability of which in at least one direction in the surface of the extent of the support body is less than that of the first stretch area.

In a second aspect of the invention, a medical referencing device comprises a marking device with at least two or more surgical marking elements, which are configured to reflect and/or emit radiation and form a marking element array for defining a reference on the body of a patient. The medical referencing device further comprises a fastening device in accordance with the first aspect, the marking device being fixable or fixed, preferably releasably, to the fastening device.

In a third aspect of the invention, a medical instrumentation comprises a fastening device in accordance with the first aspect, an optical detection unit with which images of the fastening device attached to the body part of the patient are detectable upon movement of the fastening device in space, and a data processing device adapted to be provided with image signals relating thereto by the optical detection unit. The data processing device is so configured and programmed that on the basis of the image signals it divides the support body into different deformation areas, with at least two deformation areas differing with respect to their deformation as a result of the movement of the fastening device being determinable.

BRIEF DESCRIPTION OF THE DRAWINGS

The foregoing summary and the following description may be better understood in conjunction with the drawing figures, of which.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical fastening device for noninvasively fastening a medical marking device comprising two or more marking elements to a body part of a patient, in particular, to a thigh, the fastening device comprising a support body which extends over a surface in two directions of extent aligned at an angle to each other and is adaptable in its shape to the contour of the body part, to which the marking device is fixed or fixable. The support body is elastically stretchable in the surface of its extent and comprises a first stretch area and at least one second stretch area, the stretchability of which in at least one direction in the surface of the extent of the support body is less than that of the first stretch area.

The support body of the fastening device in accordance with the invention is elastically stretchable. It can therefore be fastened under tension to the body part (for example, the femur or the tibia). As is found in practice, the skin, soft parts and muscles can thereby be compressed under the expansion of the support body. This makes it possible to reduce movement of the body parts relative to one another. The movement induced by the body part on the support body and hence on the marking device can thereby also be reduced. Moreover, the support body comprises a first and at least one second stretch area, which differ with respect to their stretchability in at least one direction in the surface of the extent of the support body. By providing stretch areas of different stretchability, it is possible to subject the skin, soft parts and muscles to different compression. As is found in practice, the inducing of movements of these body parts among one another on the support body can thereby be considerably reduced. Also, movements of skin, muscles and soft parts among one another can be substantially absorbed within the support body. The accuracy of the data obtained can be increased by the marking device being fixed to a section of the support body, which the surgeon recognizes as being subjected to a low degree of movement of its own. A stable reference of the marking device in relation to the bone, for example, the femur bone or the tibia bone, can thereby be achieved. It is preferable for the surgeon to use technical aids for this, as will be explained hereinbelow.

Preferably, the stretchability of the at least one second stretch area in two directions aligned at an angle and, in particular, transversely to each other in the surface of the extent of the support body is less than that of the first stretch area. The differences in the stretchabilities of the stretch areas can thereby be increased. As is found in practice, the accuracy of the position data obtained can thereby be increased.

It may, of course, be provided that the stretchability of the at least one second stretch area in a direction in the surface of the extent of the support body is less than the stretchability of the first stretch area, which direction is aligned at an angle to the two directions in the last-mentioned advantageous embodiment of the fastening device, in particular, which direction is a superimposition of the two directions of the last-mentioned embodiment.

The at least one direction in the surface of the extent of the support body, in which the at least one second stretch area has a higher stretchability than the first stretch area, is, for example, one of the two directions of extent of the support body. When the fastening device is applied to the thigh or to the tibia, which results in a deformation of the support body, the first direction of extent extends, for example, in the circumferential direction of the thigh or the tibia. A second direction of extent of the support body aligned transversely to the first direction of extent can extend, when the fastening device is applied to the thigh or to the tibia, for example, in its longitudinal direction.

In an advantageous embodiment of the fastening device in accordance with the invention, precisely one second stretch area is provided. Accordingly, the support body can comprise a first stretch area and a second stretch area.

It proves expedient for the first stretch area and/or the at least one second stretch area to be continuous within itself or themselves.

In a different advantageous embodiment of the fastening device, it may be provided that the first stretch area and/or the at least one second stretch area can have sections which are spatially separate from one another.

In an expedient implementation of the fastening device in practice, it is advantageous for the at least one second stretch area to surround the first stretch area. For example, the at least one second stretch area forms an enclosure for the first stretch area in the surface of the support body. The at least one second stretch area can, in particular, form an edge of the support body, which encloses the first stretch area.

The support body can, in a plan view, have a rectangular or substantially rectangular contour. For example, this can be the case when the support body is a section or component of a bandage configured by the fastening device, as will be explained hereinbelow.

In an advantageous implementation of the fastening device, it proves expedient for the first stretch area, in a plan view of the surface of the support body, to have a rectangular or substantially rectangular contour. This is advantageous, in particular, when the at least one second stretch area, as mentioned hereinabove, encloses the first stretch area and forms an edge of the support body.

In a different implementation of the fastening device, it is advantageous for the first stretch area, in a plan view of the surface of the support body, to have a tapered contour with two widening sections and a narrowing section arranged between these. Such a configuration of the fastening device is used, for example, in a thigh fastening device, in particular, in the form of a bandage. The orientation of the first stretch area with widening section-narrowing section-widening section is preferably in the longitudinal direction of the femur.

It proves particularly expedient for the support body to be a textile material in the form of a knitted fabric, a warp-knitted fabric or a woven fabric or for the support body to comprise such a textile material. This allows the stretchability of the first and the at least one second stretch area to be provided in a simple way from a manufacturing point of view and to be configured differently from each other. Thread-shaped starting material for the textile material can comprise or consist of natural and/or artificial fibers and/or elastic threads.

It is advantageous for the first stretch area and the at least one second stretch area to be joined to each other by knitting, warp-knitting or weaving and, accordingly, to be knitted, warp-knitted or woven together. This makes it possible to knit, warp-knit or weave the stretch areas and the support body in a single, coordinated manufacturing process. In particular, it is not necessary to manufacture the stretch areas separately from each other and join them together in a different way, for example, by sewing.

The different stretchability of the first stretch area and the at least one second stretch area is preferably provided by the type of knitted fabric, warp-knitted fabric or woven fabric, in particular, by the type of linking and/or the number and/or structure of the threads of the textile material. For the first and the at least one second stretch area, it is thus possible to use different weaves, in which the linkings of the threads differ from one another, whereby the stretchability can be influenced. Also the yarn density, the thread material used, especially the thread stretchability and/or the number of threads used can—by way of example and not conclusively—be different in the stretch areas, in order to influence their stretchability.

In an implementation of the fastening device in practice, it proves expedient for the first stretch area to be or comprise a knitted fabric with twill weave (especially with elastic threads) or a different weave with high double-stretch elasticity (e.g. tuck weave) and/or for the at least one second stretch area to be or comprise a knitted fabric with semi-tubular weave or a different weave with low double-stretch elasticity (e.g. right-right weave without elastic thread, Jacquard weave, Milano rib weave). A high stretchability of the first stretch area can, for example, be achieved by using elastically stretchable knitting threads in the first stretch area.

It is advantageous for the fastening device to be configured as bandage or to comprise such a bandage, which is transferable from an open released state to an applied state closed within itself, and which comprises one or more fixing elements for fixing the bandage in the applied state. The support body can form a section of the bandage to which, for example, fixing elements are attached, with which the bandage is fixable in the closed, ring-shaped applied state. The fixing elements comprise, for example, a strap, a loop or eyelet through which the strap can be passed in order to tighten the bandage or a clasp for the same purpose. Further examples of fixing elements are press-studs, a hook-and-loop fastener or an adhesive layer, for example, in order to fix the strap within itself. An advantageous implementation comprises a strap and a loop, in order that the bandage can be applied tautly to the body part, in particular, the femur, with the first and the at least one second stretch areas being stretched.

The length of the bandage in the applied state is advantageously adaptable for a positive fit on the body part. For this purpose, for example, fixing elements in the form of a strap and a loop can interact for passage of the strap therethrough. The strap can be fixed within itself, for example, by means of a hook-and-loop fastener.

In a different advantageous implementation, it is expedient for the fastening device to be configured as tubular bandage closed within itself or to comprise such a tubular bandage closed within itself. The tubular bandage, which is formed entirely or in a section thereof by the support body, can be expanded, thereby undergoing stretching, and slipped over the body part. This makes it possible to fix the tubular bandage with a positive fit on the body part and to compress the body part.

The bandage is preferably a thigh bandage. At an edge, the thigh bandage can have a recess in which the kneecap or soft tissue arranged above the kneecap can engage. This makes it possible to align the thigh bandage in a defined manner relative to the body part, here the femur. A section with low deformability of the thigh bandage can be arranged at the edge of the recess. When the bandage is applied, this section can be positioned above the tendon of the quadriceps muscle. At this point, the marking device or a marking element thereof is preferably fixed to the support body, as there is little movement within the support body above the tendon of the quadriceps muscle and a transmission of movement of body parts onto the marking device can be kept low.

The fastening device may also be of foil-shaped configuration. For example, the support body can be adhesively bonded to the patient's body.

It is expedient for the support body to have friction coefficient increasing elements on its side facing the body part. The friction coefficient increasing elements can be arranged non-uniformly on the support body. This allows skin, muscles or soft parts to be additionally tautened via the friction coefficient increasing elements. This proves advantageous, in particular, with one of the aforementioned bandages. The fastening device can be additionally stabilized on the body part in the area of the friction coefficient increasing elements without creating an arrest of blood circulation at the body part even when the fastening device is tautly applied. Preferably, it is possible to introduce movements of the body parts relative to one another via the friction coefficient increasing elements in a more targeted manner into the support body and absorb them therein, in order to reduce a transmission of movements onto the marking device.

Friction coefficient increasing elements can be arranged at the first stretch area and/or at the second stretch area.

The friction coefficient increasing elements are preferably made of a silicone material or comprise such a silicone material.

The friction coefficient increasing elements may have different shapes and/or different sizes. For example, the friction coefficient increasing elements are point-shaped, for example, approximately the size of pin heads.

At least one thread, which is worked into the aforementioned textile material, for example, knitted into a knitted fabric, can be provided as friction coefficient increasing element. The thread consists, for example, of a silicone material.

Friction coefficient increasing elements are preferably arranged along at least one edge or parallel to an edge of the support body. For example, in a bandage in the circumferential direction of the bandage, in relation to its applied state, friction coefficient increasing elements can be arranged at the edge of the support body.

It is expedient for friction coefficient increasing elements to be provided at two opposite edges of the support body extending parallel to each other. For example, friction coefficient increasing elements are present at opposite edges of the bandage along its circumferential direction in the applied state.

Alternatively or additionally, it may be provided that there are provided at one edge two sections of the support body which are provided with friction coefficient increasing elements and between which there is arranged a section of the support body which is not provided with friction coefficient increasing elements. In particular, a section of the support body without friction coefficient increasing elements can be provided at the edge of the aforementioned recess of a bandage.

In the last-mentioned advantageous embodiment, the friction between the body part, for example, the thigh, and the support body can be reduced at the section without friction coefficient increasing elements. This proves advantageous, for example, in the case of extension and flection of the leg. In the area of the section, the support body is thereby engaged to a lesser extent by the skin than a section provided with friction coefficient increasing elements. As a result, the section without friction coefficient increasing elements can prove so spatially stable on the thigh that a marking device arranged on the support body on its side facing away from the skin in the area of this section can represent a valid reference in relation to the femur bone because it can also maintain the position relative to the femur bone in the case of extension and flection of the leg.

The fastening device preferably comprises at least one holding part, which is fixed to the support body, and, expediently, the marking device or a marking element of the marking device is preferably releasably fixed or fixable with force and/or positive locking on a side of the holding part facing away from the support body. The holding part can be fixed to the first and/or to the at least one second stretch area.

As described hereinabove, in the case of a bandage, the holding part is preferably arranged at an edge or near an edge of a recess on the support body. The holding part is expediently arranged above a tendon of the quadriceps muscle when the bandage is applied to the femur in accordance with the specifications.

The holding part preferably engages the support body with a side facing the support body or is embedded in the support body. If a textile material is provided, the holding part can, for example, be embedded in the support body and thereby anchored to the support body.

It proves advantageous for the holding part to be nonrigid. A direct transmission of movements of the support body onto the marking device or the marking element can thereby be avoided.

It, therefore, proves expedient for the at least one holding part to be of deformable configuration, the deformability at a side of the holding part facing the support body preferably being greater than at a side of the holding part facing away from the support body. Accordingly, the deformability of the holding part can decrease from the support body to the marking device or the marking element and the hardness of the holding part increase. Movements within the support body can thereby be absorbed by the holding part. However, owing to its decreasing deformability, they are not transmitted or only transmitted to a slight extent to the marking device or the marking element, and so its movement can be reduced and the accuracy of the position data increased.

It may be provided that the holding part has a layer construction with two or more layers lying one on the other, with the layers having a different deformability. As mentioned hereinabove, one of the layers can be embedded in the support body, for example, in a textile material. The layers are, for example, made of a silicone material or comprise a silicone material.

Alternatively or additionally, it may be provided that the holding part has a porous structure comprising cavities, an average size of cavities in the holding part being smaller at its side facing away from the support body than at its side facing the support body. As a result, it is also possible to configure the holding part near the support body more deformable than at a distance from the support body where the marking device or the marking element is arranged.

It is conceivable for the marking device or the marking element to be directly attached to the holding part.

It proves advantageous if at the side of the holding part facing away from the support body there is fixed or embedded in the holding part a holding element to which the marking device or the marking element is fixed or fixable. For example, the holding element is embedded in one of the aforementioned layers of the holding part. The holding element can interact with a corresponding attachment element on the marking device or on the marking element, for example, by means of screwing, clamping or locking. A connection using magnets, a hook-and-loop fastener or by adhesion is also possible. As a whole, an attachment of the marking device or the marking element with positive locking and/or force locking can be provided.

As mentioned at the outset, the present invention also relates to a medical referencing device. The medical referencing device comprises a marking device with at least two or more surgical marking elements, which are configured to reflect and/or emit radiation and form a marking element array for defining a reference on the body of a patient, and a fastening device. The fastening device is a fastening device of the aforementioned kind, and the marking device is fixable or fixed, preferably releasably, to the fastening device.

The marking element array can be of rigid construction, the marking elements being firmly connected to one another and jointly fixable to the fastening device.

Alternatively, the marking element array can be of non-rigid construction, two or more marking elements being changeable in position relative to one another. For example, the marking elements are positionable separately from one another, in particular, fixable individually on the support body.

It is advantageous for the marking device to have as low a weight as possible and as small a size as possible, in particular, as low a height as possible relative to the body part. The accuracy of the position data obtained can thereby be increased.

For example, it may be provided that the marking device comprises a plate-shaped carrying element to which the marking elements are fixed, as a result of which the marking device has a low constructional height. The distance of the marking device, fixed to the fastening device, relative to the body part to be referenced can thereby be kept as small as possible.

The marking device, in particular, its marking elements, can be fixed to the aforementioned holding part, in particular, the holding element.

For this purpose, the marking device or the two or more marking elements can comprise an attachment element. Alternatively, an attachment element can be provided for fixing to the support body.

In this case, locking elements, clamping elements, hook-and-loop fasteners or magnets can, for example, be used as attachment elements.

The present invention furthermore relates to a medical instrumentation comprising a fastening device. The object mentioned at the outset is accomplished, in accordance with the invention, by an instrumentation which comprises a fastening device of the aforementioned kind and an optical detection unit with which images of the fastening device attached to the body part of the patient are detectable upon movement of the fastening device in space, and a data processing device adapted to be provided with image signals relating thereto by the optical detection unit. The data processing device is so configured and programmed that on the basis of the image signals it divides the support body into different deformation areas, at least two deformation areas differing with respect to their deformation as a result of the movement of the fastening device being determinable.

In particular, the instrumentation can support the surgeon in identifying one or more areas of little deformation, in order to fix the marking device or a marking element thereto.

Such an area of relatively little deformation can differ from the first and/or the at least one second stretch area.

However, in particular, a stretching of the support body can be regarded as "deformation" for determining the deformation areas.

For determining the deformation areas, the data processing device can comprise an image processing program which automatically determines on the basis of the image signals of the detection unit which areas of the support body undergo deformation to a relatively slight extent when the body part is moved. The image processing program can use a finite element method, for example, for this purpose.

The instrumentation expediently comprises a display unit on which the data processing device represents an image of the support body in which the deformation areas are characterized for visual distinction from one another. The different deformation areas can thereby be easily recognized by the surgeon.

Output of an indication to fix a marking device or a marking element at a deformation area, the deformation of which is less than the deformation of at least one further area of the support body is preferably possible at the display unit. The positioning of the marking device or the marking element is thereby facilitated for the surgeon.

The data processing device can use, for example, one or more colors or a surface structure of the support body for dividing the deformation areas, in particular, colors of threads or a surface structure as a result of a weave of threads of a support body configured as textile material or comprising such a textile material. Accordingly, the data processing device can, for example, divide deformation areas in which the surface of a knitted fabric does not change or only changes to a slight extent and regard such an area as deformation area of slight deformability. For this purpose, it is expedient for the textile material, in particular, the knitted fabric, to have a pattern with a high contrast. This high contrast is enabled, for example, by the color of the threads used, for example, black-white threads.

It is preferable for the data processing device to be portable and/or the display unit and/or the detection unit to be integrated in the data processing device. For example, a mobile portable device in the form of a tablet computer or a smartphone is used.

The following description of preferred embodiments of the invention will serve in conjunction with the drawings to explain the invention in greater detail.

Figure 1:
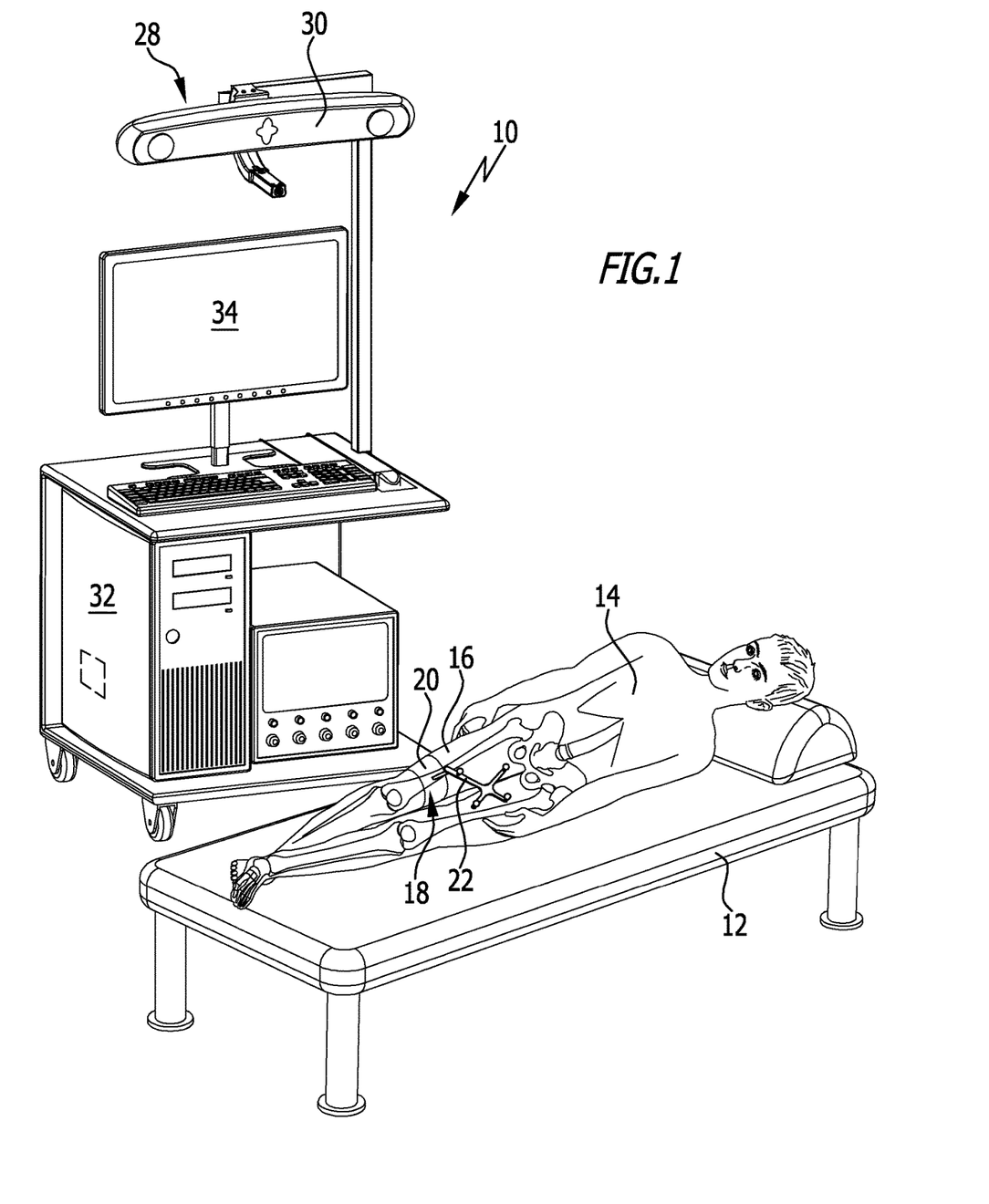
FIG. 1: shows a perspective illustration of a medical navigation system, comprising a referencing device in accordance with the invention fixed to a patient with a fastening device in accordance with the invention.
Figure 5:
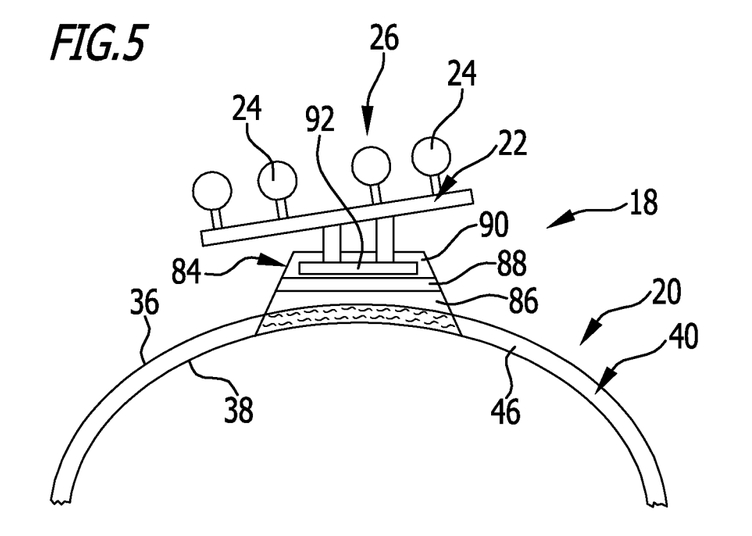
FIG. 5: shows a sectional view (in part) along line 5-5 in FIG. 4.

FIG. 1 shows a perspective illustration of a medical navigation system 10 and a patient 14 with a femur (in this case, thigh) 16 lying on an operating table 12. The navigation system 10 comprises an advantageous embodiment, denoted by reference numeral 18, of a referencing device in accordance with the invention. The referencing device 18 comprises an advantageous embodiment of a fastening device 20 in accordance with the invention which is noninvasively fixable to the femur 16 and a medical marking device 22. The marking device 22 is configured as so-called "rigid body" with marking elements 24 (FIG. 5). The marking elements 24 are arranged stationarily relative to one another and form a rigid marking element array 26 on the femur 16.

When the femur 16 moves in space, the marking device 22 also moves. Radiation reflected by the marking elements 24, which is emitted by a detection device 28 of the navigation system 10, can be detected by the detection device 28. The detection device 28 comprises a stereo camera 30 for this purpose. Position data of the detection device 28 are transmitted to a data processing device 32 of the navigation system. The data processing device 32 calculates on the basis of the position data the position and the orientation of the marking device 22 and hence the femur 16 in space. Information relating thereto can be represented on a display device 34 of the navigation system 10.

The navigation system 10 with the referencing device 18 can be used, for example, for navigation-supported implantation of an artificial knee joint. For reasons explained hereinbelow, in particular, preoperative, intraoperative and postoperative use of the referencing device 18 is possible.

Figure 2:
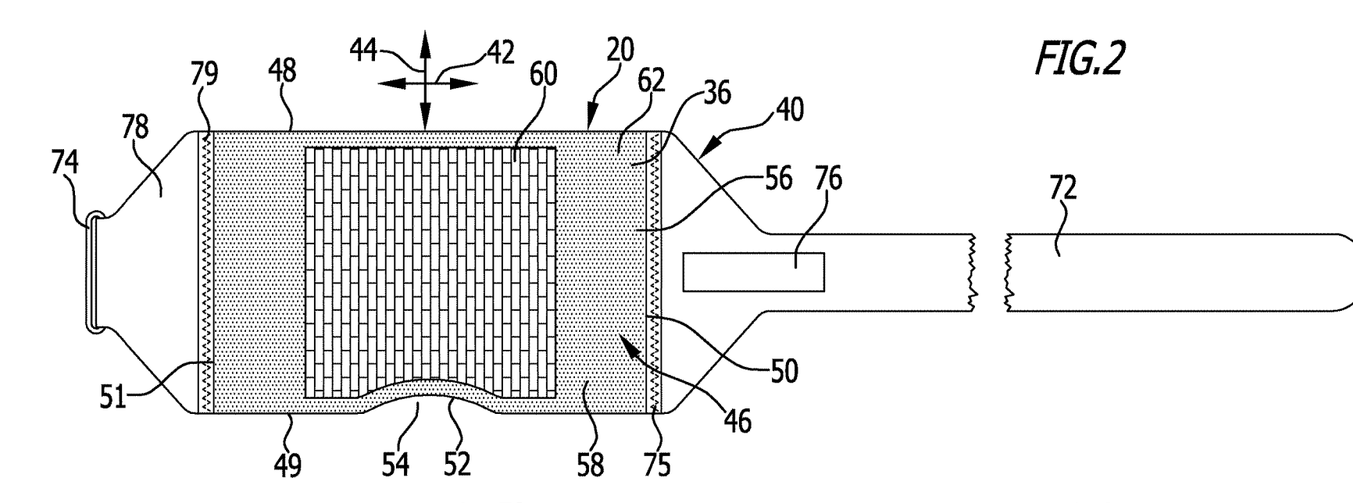
FIG. 2: shows a plan view of a first side of the fastening device from FIG. 1, configured as bandage.
Figure 3:
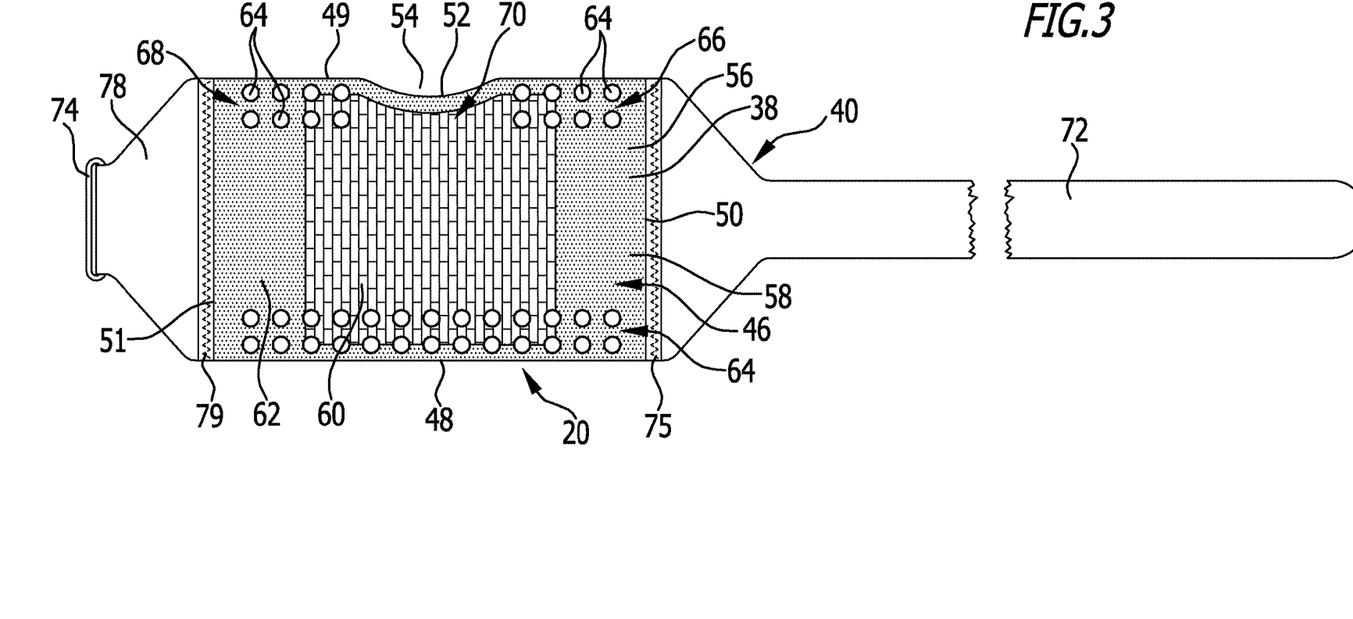
FIG. 3: shows a plan view of a second side of the fastening device located opposite the first side.

FIGS. 2 and 3 show the fastening device 20 schematically in a plan view of a first side (upper side 36 hereinbelow) and a second side (underside 38 hereinbelow). When the fastening device 20 and the referencing device 18 are used in accordance with the specifications, the underside 38 faces the femur 16, and the upper side 36 faces away from the femur 16.

The fastening device 20 is configured, in this case, as bandage 40, in particular, as compression bandage. The bandage 40 comprises a support body 46, extending over a surface in two directions of extent 42, 44 aligned transversely to each other, for the marking device 22. The support body 46 is changeable in shape and adaptable to the contour of the femur 16 when the bandage 40 is applied thereto. The support body 46, like the bandage 40 in its entirety, can thus be applied with a positive fit to the femur 16 and surround it. When the bandage 40 is applied to the femur 16 with the support body 46 undergoing deformation during use in accordance with the specifications, the direction of extent 42 runs in the circumferential direction of the femur 16 and the direction of extent 44 in the longitudinal direction of the femur 16.

The support body 46 is of substantially rectangular shape in a plan view with two longitudinal sides 48, 49 extending parallel to each other in the direction of extent 42 and transverse sides 50, 51 in the direction of extent 44. The longitudinal side 49 has an arcuate curvature 52 in its middle section, and so a recess 54 is arranged at the edge of the support body 46 in the area of the curvature 52.

In this case, the support body 46 is a textile material 56, configured as knitted fabric 58. The support body 46 and hence the bandage 40 can therefore be simply and cost-effectively produced from a manufacturing point of view. In this case, the knitted fabric 58 has two areas of different weave, and owing to the different weave and the threads used, the support body 46 therefore has different characteristics in areas thereof.

In particular, the knitted fabric 58 is made such that the support body 46 is elastically stretchable in the surface of its extent in two directions aligned transversely to each other, in particular, in the direction of extent 42 and the direction of extent 44. When applying the bandage 40, the support body 46 can be stretched in order to compress the femur 16, as explained in more detail hereinbelow.

The knitted fabric 58 has a first stretch area 60 which, in a plan view of the support body 46, has a substantially rectangular shape. The stretch area 60 is located at the center of the support body 46 and is surrounded by a second stretch area 62. The stretch area 62 encloses the stretch area 60 and forms an edge for it. The stretch area 62, furthermore, forms the longitudinal sides 48, 49 and the transverse sides 50, 51.

Owing to the configuration of the knitted fabric 58, the stretch areas 60, 62 are connected to each other in a simple way from a manufacturing point of view and in one operation by knitting.

In this case, the first stretch area 60 is a knitted fabric with high double-stretch elasticity, for example, with twill weave, which, in particular, has elastic knitting threads. The stretch area 62 is a knitted fabric with semi-tubular weave with threads of lower elasticity. As a result, the stretch area 60 has in both directions of extent 42, 44 (and in a direction resulting from a superimposition of the directions of extent 42, 44 and respectively aligned at an angle to these in the surface of the support body 46) a greater stretchability than the stretch area 62. The stretchability of the stretch area 60 is greater in the direction of extent 44 than in the direction of extent 42.

On the underside 38, the support body 46 has a plurality of friction coefficient increasing elements 64 (hereinbelow, for the purpose of simplification, friction elements 64). In this case, the friction elements 64 are point-shaped and, for example, approximately the size of a pin head. The friction elements 64 are preferably made of a silicone material.

The support body 46 comprises friction elements 64 at the edge which has the longitudinal side 48. The friction elements 64 extend in a double row parallel to the longitudinal side 48 and are uniformly spaced from one another. The friction elements extend substantially over the entire length of the support body 46 and are arranged on both stretch areas 60, 62.

At the opposite edge forming the longitudinal side 49, the support body 46 has a first section 66 and a second section 68, each with friction elements 64, and a section 70 lying between these, which is free of friction elements 64. The section 66 is arranged, in the direction of extent 42, between the recess 54 and the transverse side 50, and the section 68 between the recess 54 and the transverse side 51. The section 70 extends somewhat beyond the length of the recess 52 at the center of the support body 46. At each section 66, 68, the friction elements 64 extend in a double row parallel to the longitudinal side 49 and are respectively arranged equidistantly from one another on the support body 46.

The friction elements 64 make it possible to increase the friction between the bandage 40 and the femur 16 locally. In the area of the section 70, the friction is specifically kept low.

Figure 4:
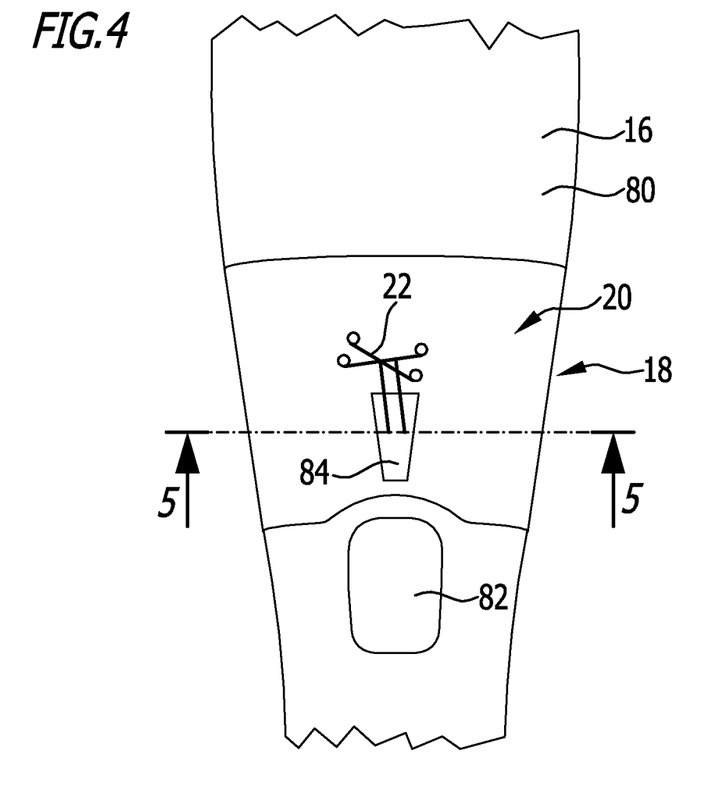
FIG. 4: shows schematically a thigh of the patient, to which the referencing device is fixed.

The bandage 40 is a bandage which is adjustable in size. From an open released state shown in FIGS. 2 and 3, it is transferable to an applied state in which the bandage 40 is closed within itself (FIGS. 1, 4, 5). For this purpose, the bandage 40 has fixing elements, namely a strap 72 and an eyelet 74 interacting therewith. The strap 72 is fixed to the transverse side 50 via a stiffening element 75 and extends along the direction of extent 42 (when the bandage 40 is laid flat).

The stiffening element 75 comprises, for example, a fabric tunnel with a helical spring or strip made, for example, of plastic, arranged therein. Near the transverse side 50, there is provided on the strap 72 a fixing element in the form of a hook-and-loop fastener 76, to which the strap 72 can be adherently attached in a manner closed within itself.

The eyelet 74 is attached to a side of a holding section 78, which is connected at the opposite side via a stiffening element 79 at the transverse side 51 to the support body 46. The stiffening element 79 corresponds in form and function to the stiffening element 75.

To transfer the bandage 40 to the applied state on the femur 16, the underside 48 is noninvasively positioned on its skin 80 (FIG. 4). The bandage 40 is preferably stretched in the direction of extent 42, counter to the elasticity of the stretch areas 60, 62. The bandage 40 is preferably positioned on the femur 16 such that soft tissue above the kneecap 82 engages the recess 54.

In the applied state, the bandage 40 is fixed by the strap 72 being guided through the eyelet 74, with the bandage 40 being tautened, and attached within itself to the hook-and-loop fastener 46. The stiffening elements 75, 79 ensure that the bandage maintains its shape in the direction of extent 44 and the support body does not taper due to the tautening.

When the soft tissue above the kneecap 82 engages the recess 54, the stretch area 60, in particular, in the area of the section 70 free of friction elements 64, is arranged above the tendon of the quadriceps muscle of the femur 16.

The bandage 40 and hence the referencing device 18 are noninvasively fixable to the femur 16 in a patient-friendly and user-friendly way. In the applied state, the bandage 40 compresses the femur 16. Movements of skin, soft tissue and muscles relative to one another and relative to the femur bone are thereby restricted. Consequently, the ability of the bandage 40 to move relative to the femur 16 and, in particular, to the femur bone is also reduced.

Also, relative movements of skin, soft tissue and muscles which do occur can be substantially absorbed within the support body 46. For this purpose, the manufacture of the support body 46 as knitted fabric 58 with the stretch areas 60, 62, which differ with respect to their stretchability in at least one of the directions of extent 42, 44, proves particularly advantageous. The stretch areas 60, 62 are knitted such that movements within the femur 16 are to a large extent absorbed by the support body 46. In particular, at the first stretch area 60 at the center thereof (in relation to the direction of extent 42), which comprises the section 70 free of friction elements 64, particularly little movement occurs within the support body 46. The friction elements 64 and their arrangement on the support body 46 improve by way of the specific compression of the femur 16 the capacity of the bandage 40 to specifically introduce movements into the support body 46.

The provision of the section 70 free of friction elements 64 has, as mentioned hereinabove, the advantage that the friction between the femur 16 and the bandage 40 can be kept low locally. For example, the skin 80 at the section 70 rubs only to a slight extent against the support body 46 during extension and flection of the leg, and so the support body 46 is not engaged or only engaged to a slight extent by a displacement of soft parts. A marking device on the upper side 36 at or near the section 70 can, therefore, form a valid reference whose position relative to the femur bone can also be maintained during extension or flection of the leg. For this purpose, it is also advantageous for the support body 46 to have a greater stretchability along the direction of extent 44 than along the direction of extent 42.

If the kneecap 82 or soft tissue above the kneecap 82 is arranged in the area of the recess 54 and the section 70 above the tendon of the quadriceps muscle, the movement of the support body 46 in this area is particularly low. This is also a consequence of the relatively low movability of the tendon of the quadriceps muscle relative to other soft tissue and other muscles in the femur 16.

For this reason, the fastening device 20 comprises at the section 70 a holding part 84 to which the marking device 22 is fixable. The holding part 84 is not shown in FIGS. 1 to 3.

The holding part 84 is of prismatic shape, approximately forming a truncated pyramid, and is fixed to the support body 46, in particular, to the stretch area 60. The holding part 84 is of multilayer construction with a first layer 86, a second layer 88 and a third layer 90. In this case, the layers 86 to 90 are, for example, made of a silicone material. It is expedient if they have different deformabilities, with the deformability preferably decreasing from the layer 86 via the layer 88 to the layer 90. Movements still occurring at the support body 46 can thereby be absorbed within the holding part 84 and are only transmitted to a slight extent or are not transmitted to the marking device 22. Via the layer 86, the holding part 84 engages the knitted fabric 58 of the support body 46 and is partially embedded therein, whereby the holding part 84 is fixed to the support body 46.

There is fixed to the layer 90 a holding element 92, to which the marking device 22 is fixed or, in particular, releasably fixable. In this case, the holding element 92 is embedded, for example, cast in the layer 90. The marking element array 26 can be fixed, for example, by screwing, clamping, locking, adhering, by a hook-and-loop fastener or the like with force and/or positive locking to the holding element 92.

The possibility of noninvasive fastening of the referencing device 18 to the patient 14 results in a patient-friendly possibility of tracking a body part such as, for example, the femur 16, with the navigation system 10 in space. As mentioned hereinabove, preoperative, intraoperative and postoperative use is possible. In spite of the fastening which is gentle on the patient, a sufficiently accurate reference can be achieved owing to the configuration of the fastening device 20, as explained hereinabove.

Further preferred embodiments of fastening devices and referencing devices in accordance with the invention will be discussed hereinbelow. Largely identical reference numerals will be used for features and components which are the same or have the same effect.

Figure 6:
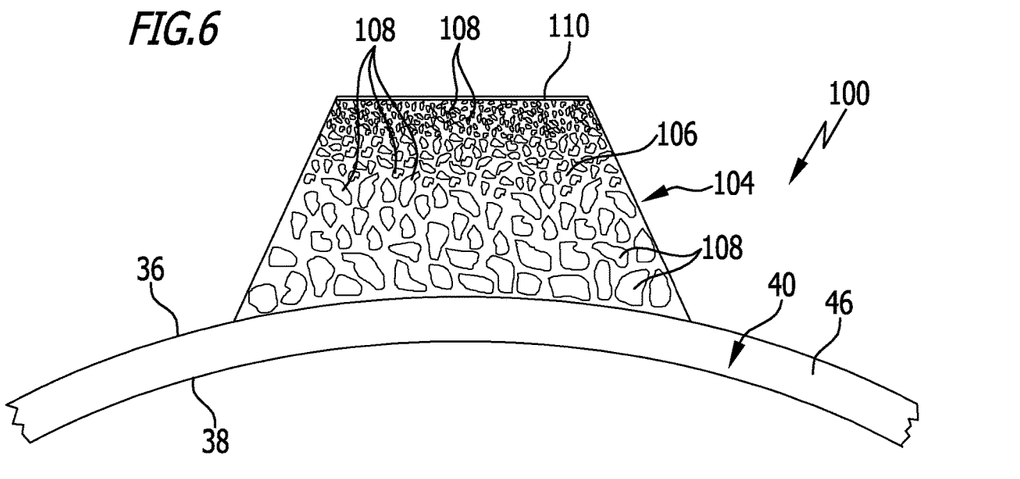
FIG. 6: shows an illustration corresponding to FIG. 5 in a different embodiment of a fastening device and a referencing device.

FIG. 6 shows schematically in a way similar to FIG. 5 a sectional illustration through a second preferred embodiment of a fastening device with reference numeral 100. The fastening device 100 comprises the bandage 40. Attached to the bandage 40 is a holding part 104 which corresponds in its function to the holding element 92. A marking device, not shown in the drawings, can be fixed or, in particular, releasably attached to the holding part 104, for example, by screwing, clamping, locking, adhering or by a hook-and-loop fastener.

The holding part 104 is fixed to the upper side 36 and comprises a porous body 106. The body 106 has a large number of cavities 108. The body 106 is configured such that the average size of the cavities 108 decreases from the side of the holding part 104 facing the support body 46 to the side of the holding part 104 facing away from the support body 46. In particular, the average size can decrease continuously. As a result, the deformability of the holding part 104 decreases from the side facing the support body 46 to the side facing away from the support body 46, and the holding part 104 is softer at the support body 46 than at a distance from it. As with the holding part 84, it is thus possible to absorb movements of the support body 46 within the holding part 104, whereby these are not transmitted or are only transmitted to a slight extent to a marking device which is fixable (not shown) to a coupling point 110 at the side of the holding part 104 facing away from the support body 46. For example, the marking device 22 is used.

Figure 7:
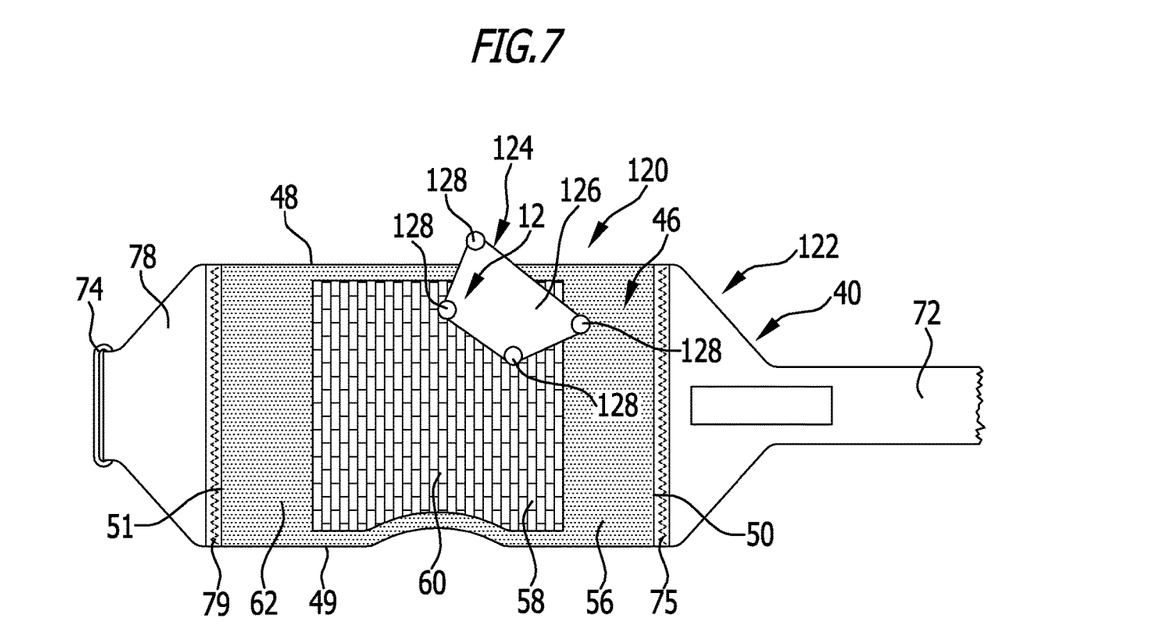
FIG. 7: shows a plan view of a further embodiment of a fastening device and a referencing device.

FIG. 7 shows a further referencing device 120 with a fastening device 122 and a marking device 124. The fastening device 122 is, apart from the holding part 84 not being provided, identical in configuration to the fastening device 20.

In this case, the marking device 124 is of compact construction and has a plate-shaped carrying element 126 of approximately trapezoidal shape and marking elements 128 fixed to its corners. These form a rigid marking element array 126. The marking device 124 has, in particular, a low constructional height and is relatively light. Owing to reduced inertia, relative movement of the marking device 124 and the fastening device 122 is particularly low. Owing to the low constructional height, even relative movements of the marking device 124 and the support body 46 result in only slight falsifications of position data, and, therefore, a high accuracy of position data when tracking the femur 16 in space is achievable with the referencing device 120. Constructionally, the marking device 124 can be easily fixed to the support body 46, for example, by adhesion or by a hook-and-loop fastener.

Figure 8:
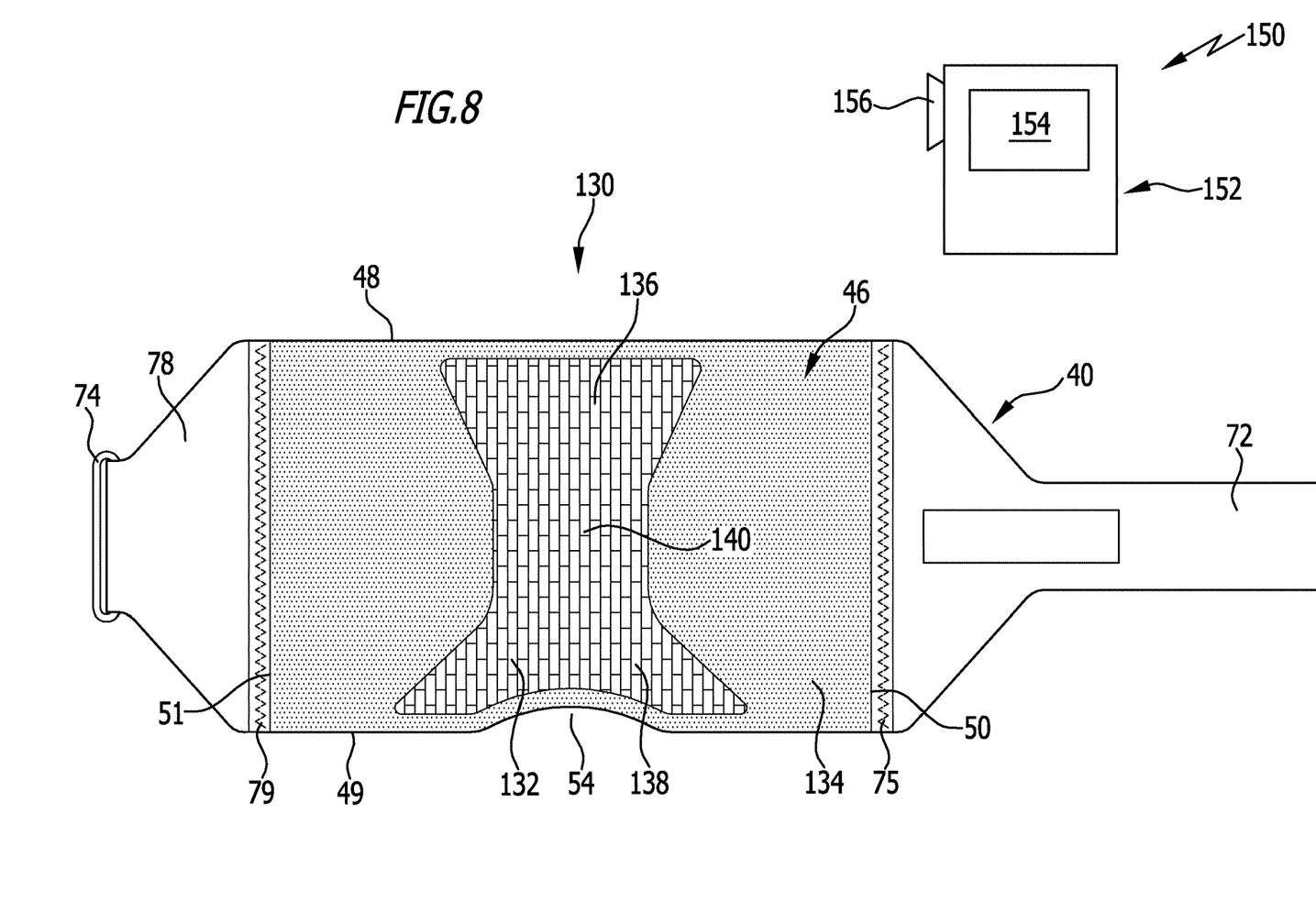
FIG. 8: shows a plan view of a further embodiment of a fastening device.

FIG. 8 represents in a way corresponding to FIG. 2 a further fastening device 130. The fasting device 130 is largely identical to the fastening device 20. It can comprise the holding part 84 or the holding part 104 or, like the fastening device 122, have no holding part. The marking device 124 can, for example, interact with the fastening device 130 to form a referencing device.

In the fastening device 130, two stretch areas 132, 134 are provided, which correspond to the stretch areas 60, 62. The stretch area 134 surrounds the stretch area 132. The stretch area 132 has, in a plan view of the support body 46, a tapered contour with two widening sections 136, 138 arranged at a distance from each other. A narrowing section 140 is arranged between these. The sections 136 to 140 are arranged along the direction of extent 42 at the center between the transverse sides 50, 51. In the direction of extent 44, the widening section 136 is adjacent to the longitudinal side 48, and the widening section 138 adjacent to the longitudinal side 49.

The fastening device 130 and also the fastening device 122 likewise have friction elements at their respective underside, not shown in the drawings.

The advantages achievable as explained in conjunction with the fastening device 30 can also be achieved with use of the fastening devices 100, 122 and 130.

In addition to the fastening device 130, FIG. 8 shows a medical instrumentation 150 which, in this case, comprises the fastening device 130 as well as a data processing device 152. The data processing device 152 is preferably hand-holdable and portable, for example, in the form of a tablet computer. Accordingly, the data processing device 152 can preferably include a display unit 154 as integral component.

There is also integrated in the data processing device 152 an optical detection unit 156, shown schematically in FIG. 8, which, in particular, comprises a digital camera.

When the instrumentation 150 is in use, the detection unit 156 is directed at the bandage 40 fixed to the femur 16, in particular, its support body 46. Image signals which are provided by the detection unit are examined by the data processing device 152 as to whether the support body 46 can be divided into different deformation areas. As a result of movement of the femur 16 and associated displacements of skin, soft tissue, muscles and femur bone relative to one another and possible movement of the bandage 40 on the femur 16, the support body 46 may have areas of different deformation. These areas may differ from the stretch areas 132, 134. With the fastening device 130, the data processing device 152 determines, for example, that an area of the support body 46 with little deformation is, however, located at the stretch area 132 near the recess 54, as already explained hereinabove.

To determine the deformation areas, the data processing device 152 can use, for example, one or more colors or a surface structure of the support body 46, for example, colors of threads of the support body 46 or a surface structure owing to the weave, for example, the different weaves of the deformation areas 136, 140. Accordingly the data processing device 152 can include an image processing program which automatically determines on the basis of the image signals which area of the support body 46 deforms to a relatively slight extent. For example, a finite element method is used for this purpose.

An image of the support body 46 can be shown to the operator on the display unit 154. The different deformation areas are preferably characterized in this image. It is expedient for the operator to be given an indication as to where on the support body 46 a marking device, for example, the marking device 124, should be advantageously placed in order to obtain as stable a reference as possible.

The integrated data processing device 152 can, of course, also be used with the fastening devices 100, 122 and 20. For example, with the referencing device 120, the marking device 124 was placed at the position shown in FIG. 7 on the fastening device 122 because this position has proven suitable for a stable reference.

What is claimed is:

1. Medical fastening device for noninvasively fastening a medical marking device comprising two or more marking elements to a body part of a patient, the medical fastening device comprising:
    a support body which extends over a surface in two directions of extent aligned at an angle to each other and which is adaptable in shape to a contour of the body part,
    the support body being elastically stretchable in a surface of extent and comprising a first stretch area and at least one second stretch area, the stretchability of the at least one second stretch area in at least one direction in the surface of the extent of the support body is less than the stretchability of the first stretch area, and
    at least one holding part fixed to the first stretch area of the support body,
    wherein the marking device or a marking element of the marking device is fixed or fixable with at least one of force locking and positive locking on a side of the holding part facing away from the support body.

2. Fastening device in accordance with claim 1, wherein the stretchability of the least one second stretch area in two directions aligned at an angle and, in particular, transversely to each other in the surface of the extent of the support body is less than the stretchability of the first stretch area.

3. Fastening device in accordance with claim 1, wherein the at least one second stretch area surrounds the first stretch area.

4. Fastening device in accordance with claim 1, wherein the support body, in a plan view, has a rectangular or substantially rectangular contour.

5. Fastening device in accordance with claim 1, wherein the first stretch area, in a plan view of the surface of the support body, has a rectangular or substantially rectangular contour or wherein the first stretch area, in a plan view of the surface of the support body, has a tapered contour with two widening sections and a narrowing section arranged between the two widening sections.

6. Fastening device in accordance with claim 1, wherein the support body is a textile material in a form of a knitted fabric, a warp-knitted fabric or a woven fabric or wherein the support body comprises such a textile material.

7. Fastening device in accordance with claim 6, wherein the first stretch area and the at least one second stretch area are joined to each other by knitting, warp-knitting or weaving.

8. Fastening device in accordance with claim 6, wherein the different stretchability of the first stretch area and the at least one second stretch area is provided by the type of knitted fabric, warp-knitted fabric or woven fabric, in particular, by at least one of a type of linking, a number of the threads of the textile material and a structure of the threads of the textile material.

9. Fastening device in accordance with claim 6, wherein the first stretch area is or comprises a knitted fabric with twill weave and/or wherein the at least one second stretch area is or comprises a knitted fabric with semi-tubular weave.

10. Fastening device in accordance with claim 1, wherein the fastening device is configured as a bandage or comprises a bandage, which is transferable from an open released state to an applied state closed within itself, and which comprises one or more fixing elements for fixing the bandage in the applied state.

11. Fastening device in accordance with claim 10, wherein a length of the bandage in the applied state is adaptable for a positive fit on the body part.

12. Fastening device in accordance with claim 1, wherein the fastening device is configured as a tubular bandage closed within itself or comprises such a tubular bandage closed within itself.

13. Fastening device in accordance with claim 1, wherein the support body has friction coefficient increasing elements on a side of the support body facing the body part.

14. Fastening device in accordance with claim 1, wherein the at least one holding part is of a deformable configuration, the deformability at a side of the holding part facing the support body preferably being greater than at a side of the holding part facing away from the support body.

15. Fastening device in accordance with claim 14, wherein the holding part has a layered construction with two or more layers lying one on the other, with the layers having a different deformability.

16. Fastening device in accordance with claim 1, wherein the holding part has a porous structure comprising cavities, an average size of cavities in the holding part being smaller at a side of the holding part facing away from the support body than at a side of the holding part facing the support body.

17. Medical referencing device, comprising:
    a marking device with at least two or more surgical marking elements, which are configured to reflect and/or emit radiation and form a marking element array for defining a reference on a body of a patient, and
    a fastening device comprising:
        a support body which extends over a surface in two directions of extent aligned at an angle to each other and which is adaptable in shape to a contour of a body part,
        the support body being elastically stretchable in a surface of extent and comprising a first stretch area and at least one second stretch area, the stretchability of the at least one second stretch area in at least one direction in the surface of the extent of the support body is less than the stretchability of the first stretch area, and at least one holding part fixed to the first stretch area of the support body, wherein the marking device or a marking element of the marking device is fixed or fixable with at least one of force locking and positive locking on a side of the holding part facing away from the support body.

18. Referencing device in accordance with claim 17, wherein the marking element array is of rigid construction, the marking elements being firmly connected to one another and jointly fixable to the fastening device or wherein the marking element array is of non-rigid construction, two or more marking elements being changeable in position relative to one another.

19. Medical instrumentation, comprising:
a fastening device, comprising:
   a support body which extends over a surface in two directions of extent aligned at an angle to each other and is adaptable in shape to a contour of a body part, to which a marking device is fixed or fixable,
   wherein the support body is elastically stretchable in a surface of extent and comprises a first stretch area and at least one second stretch area, the stretchability of the at least one second stretch area in at least one direction in the surface of the extent of the support body is less than the stretchability of the first stretch area,
an optical detection unit with which images of the fastening device attached to the body part of the patient are detectable upon movement of the fastening device in space, and
a data processing device adapted to be provided with image signals relating thereto by the optical detection unit,
the data processing device being so configured and programmed that on the basis of the image signals it divides the support body into different deformation areas, with at least two deformation areas differing with respect to their deformation as a result of the movement of the fastening device being determinable.

20. Medical instrumentation in accordance with claim 19, wherein the fastening device comprises at least one holding part, which is fixed to the support body, and wherein the marking device or a marking element of the marking device is fixed or fixable with at least one of force locking and positive locking on a side of the holding part facing away from the support body.

21. Medical fastening device for noninvasively fastening a medical marking device comprising two or more marking elements to a body part of a patient, the medical fastening device comprising:
a support body which extends over a surface in two directions of extent aligned at an angle to each other and which is adaptable in shape to a contour of the body part,
the support body being elastically stretchable in a surface of extent and comprising a first stretch area and at least one second stretch area, the stretchability of the at least one second stretch area in at least one direction in the surface of the extent of the support body is less than the stretchability of the first stretch area, and
at least one holding part fixed to the support body, wherein:
the marking device or a marking element of the marking device is fixed or fixable with at least one of force locking and positive locking on a side of the holding part facing away from the support body, and
the at least one holding part is of a deformable configuration, the deformability at a side of the holding part facing the support body being greater than at a side of the holding part facing away from the support body.

22. Medical fastening device for noninvasively fastening a medical marking device comprising two or more marking elements to a body part of a patient, the medical fastening device comprising:
a support body which extends over a surface in two directions of extent aligned at an angle to each other and which is adaptable in shape to a contour of the body part,
the support body being elastically stretchable in a surface of extent and comprising a first stretch area and at least one second stretch area, the stretchability of the at least one second stretch area in at least one direction in the surface of the extent of the support body is less than the stretchability of the first stretch area, and
at least one holding part fixed to the support body, wherein:
the marking device or a marking element of the marking device is fixed or fixable with at least one of force locking and positive locking on a side of the holding part facing away from the support body, and
the holding part has a porous structure comprising cavities, an average size of cavities in the holding part being smaller at a side of the holding part facing away from the support body than at a side of the holding part facing the support body.

* * * * *